United States Patent [19]

Patel et al.

[11] Patent Number: 5,413,935
[45] Date of Patent: May 9, 1995

[54] PROCESS FOR SELECTING AN ENANTIOMER OF A HYDROXY LACTONE USING PSEUDOMONAS LIPASE

[75] Inventors: Ramesh N. Patel, Bridgewater; Clyde G. McNamee, Lawrenceville; Laszlo J. Szarka, East Brunswick, all of N.J.

[73] Assignee: E. R. Squibb & Sons, Inc., Princeton, N.J.

[21] Appl. No.: 106,182

[22] Filed: Mar. 24, 1993

Related U.S. Application Data

[63] Continuation of Ser. No. 690,456, Apr. 24, 1991, abandoned.

[51] Int. Cl.$^6$ ............................................. C12P 41/00
[52] U.S. Cl. ............................. 435/280; 435/874; 435/876; 435/877
[58] Field of Search ............... 435/280, 120, 125, 874, 435/876, 877

[56] References Cited

U.S. PATENT DOCUMENTS

| | | | |
|---|---|---|---|
| 3,684,477 | 8/1972 | Blumbergs et al. | 71/67 |
| 4,897,490 | 1/1990 | Sit et al. | 548/253 |
| 5,084,392 | 1/1992 | Miyazawa et al. | 435/280 |

OTHER PUBLICATIONS

Jones JB, Tetrahedron 42: 3351–3403 (1986).
Kazlauskas R, J. Org. Chem. 56: 2656–65 (1991).
Okumura, S et al, BBA 575: 156–165 (79).
Hills, M. et al., BBA 1042: 237–240 (1990).
Zaks et al, Proc. Natl. Acad. Sci 82: 3192–3196 (1985).
Fitzpatrick et al, J. Am. Chem Soc. 113:3166–3171 (1991).
Hsu et al, Tet. Lett. 31: 6403–6406 (1990).
V. C. J. Sih et al., Angew. Chem., 96, 556–565, 1984.
M. J. Barton et al., Enzyme Microb. Technol., 12, 577–583, 1990.

*Primary Examiner*—Marian C. Knode
*Assistant Examiner*—Sandra Saucier
*Attorney, Agent, or Firm*—Timothy J. Gaul

[57] ABSTRACT

An enantiomerically pure compound of the formula

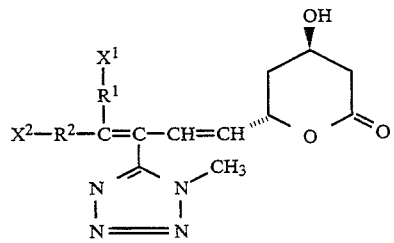

is prepared when the associated racemic mixture is reacted with an acrylating agent $R^3$—C(O)—O—R in the presence of a microorganism or enzyme derived therefrom capable of catalyzing transesterification of an alcohol. $X^1$ and $X^2$ are each independently halogen, R is alkyl, $R^1$ and $R^2$ are each independently alkyl, cycloalkyl, aralkyl or aryl and $R^3$ is alkyl, cycloalkyl, aryl or aralkyl.

13 Claims, No Drawings

PROCESS FOR SELECTING AN ENANTIOMER OF A HYDROXY LACTONE USING PSEUDOMONAS LIPASE

This is a continuation of application Ser. No. 690,456 filed on Apr. 24, 1991, now abandoned.

BACKGROUND OF THE INVENTION

A compound of the formula

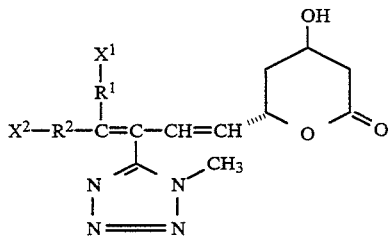

is described in U.S. Pat. No. 4,897,490. Compound I is useful, inter alia, as a cholesterol-lowering agent, as described in the above patent. The enantiomer of compound I having the formula

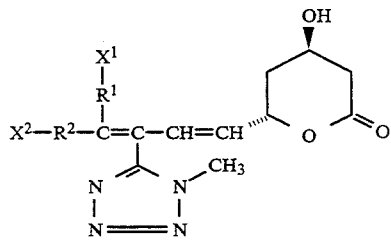

is more active in lowering blood serum cholesterol.

SUMMARY OF THE INVENTION

In accordance with the present invention, a novel process for preparing optically active compound II is described, wherein $X^1$ and $X^2$ are each independently halogen and $R^1$ and $R^2$ are each independently alkyl, cycloalkyl, aralkyl or aryl. The present process comprises reacting a racemic mixture of compound II with a compound of the formula

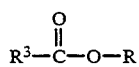

wherein R is alkyl, cycloalkyl, aryl or aralkyl, in the presence of an enzyme or microorganism capable of catalyzing the selective transesterification of compounds of formula II to provide a solution comprising separable desired enantiomeric unreacted alcohol of formula I and undesired enantiomeric ester of the formula IV

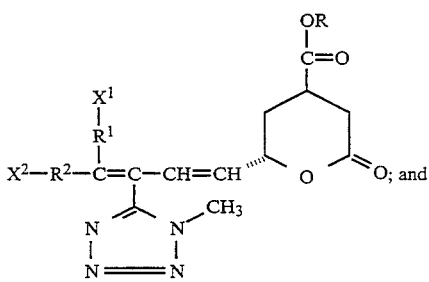

recovering the resulting non-esterified desired enantiomer of formula I.

DETAILED DESCRIPTION OF THE INVENTION

The following definitions apply to the terms used throughout this specification either individually or as part of another group, unless otherwise limited in specific circumstances.

The term "alkyl" as used herein refers to straight or branched chain hydrocarbon groups of 1 to 12 carbon atoms, preferably 1 to 6 carbon atoms.

The term "cycloalkyl" as used herein refers to groups containing 5 to 7 carbon atoms.

The term "aryl" as used herein refers to monocyclic or bicyclic aromatic groups having from 6 to 10 carbon atoms in the ring portion, such as phenyl, naphthyl, and substituted phenyl or naphthyl having substituents such as nitro, halogen, methyl or alkoxy groups on the aromatic ring.

The terms "halogen" and "halo" refer to fluorine, chlorine, bromine and iodine.

In accordance with the present invention, it has been found that acetate of formula III, in the presence of lipases or esterases (or microorganisms capable of producing same), are capable of catalyzing the stereoselective transesterification of alcohols such as compound II. This process produces esters in the undesired enantiomeric form having the formula IV, and the resulting "by-product" is in fact a high yield of optically pure unreacted desired enantiomers of formula I.

Compound III used in the present process can be any esterifying compound (e.g., acetate) capable of esterifying compounds of formula II. In preferred embodiments, isopropenyl acetate or vinyl acetate were used; each provided optical purity in excess of 98% at reaction yield of between 40 to 49%.

The present process can be carried out in an organic solvent. Typical solvents suitable for use in the present process include, but are not limited to, 1,1,2-trichloro-1,2,2-trifluoroethane, toluene, cyclohexane, benzene, hexane, heptane, isooctane, octane, methylethyl, ketone, methyl isobutyl ketone and the like.

The enzyme or microorganism used in the present process can be any enzyme or microorganism capable of catalyzing the stereoselective esterification of alcohols such as compounds of formula II. Various enzymes, such as esterases and lipases, regardless of origin or purity, are suitable for use in the present invention. The enzyme can be in the form of a mixture of animal and plant enzyme, cells of microorganisms, crushed cells or extracts of cells.

Typical genuses of microorganism suitable as sources of catalyzing enzymes include *Mucor, Escherichia,*

*Staphlococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevibacterium, Enterobacter, Chromobacterium, Arthrobacter, Microbacterium, Mycobacterium, Saccharomyces, Penicillium, Botrytis, Chaetomium, Ophiobolus, Cladosporium* and the like.

Commercially available enzymes suitable for use in the present invention include lipases, such as Amano P (*Pseudomonas fluorescens*) which is preferred, Amano AY-30 (*Candida cylindracea*), Amano N (*Rhizopus niveus*), Amano R (*Penicillium sp.*), Amano FAP (*RhizopuUs oryzae*), Amano AP-12 (*Aspergillus niger*), Amano MAP (*Mucor meihei*), Amano GC-4 (*Geotrichum candidum*), Sigma L-0382 (porcine pancrease ), Sigma L-3001 (Wheat germ ), Sigma L-1754 (*Candida cylindracea*), Sigma L-0763 (*Chromobacterium viscosum*) and Amano K-30 (*Aspergillus niger*). Additionally, enzymes derived from animal tissue include esterase from pig liver, α-chymotrypsin and pancreatin from pancreas.

Specific microorganisms suitable for use in the present process include *Pseudomonas fluorescens, Pseudomonas putida, Pseudomonas ovalis, Escherichia coli, Staphylococcus aureus, Alicaligenes faecalis, StreptomUces, griseus, StreptomUces clavugligerus, nocardia erthropolis, Nocardia asteraides, Mycobacterium phlei, Agrobacterium radiobacter, Aspergillus niger, Rhizopus oryzae* and the like.

To carry out the process of the present invention, compound III is added to the desired organic solvent. The enzyme (or microorganism containing same) is added thereto. Typically, the enzyme is used in free state or is adsorbed onto a suitable carrier, e.g., diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. A carrier immobilizes the enzyme, which controls the enzyme particle size and prevents aggregation of the enzyme particles when used in an organic solvent. This can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. The reaction solution typically contains between about 5 and 250 mg of racemic starting material per ml of solvent. The enzyme added to the reaction solution may be present in preferred concentrations ranging from about 5 to about 200 mg of enzyme per ml of solvent. While it is desirable to use the least amount of enzyme possible, the amount of enzyme required will vary depending upon the specific activity of the enzyme used.

When the reaction is conducted in an organic solvent, small amounts of water may be added to the reaction mixture. The water added to the reaction mixture may be present in concentrations ranging from about 0.01% to about 1% of water in solvent, or solvent saturated with water, and preferably is present in an amount of about 0.05 to 0.5%. Incubation of the reaction solution can be at a temperature between about 4° and about 60° C. and is preferably carried out at 30° to 50° C. The reaction time can be appropriately varied depending upon the amount of enzyme used and its specific activity. Typical reaction times at 37° C. for optical purities of 95 percent and above are at least about 8 hours and can range up to about 18 hours for greater conversions and higher optical purities, e.g., optical purities exceeding 98 percent. Reaction times can be reduced significantly by increasing the reaction temperature and/or increasing the amount of enzyme added to the reaction solution. Desired enantiomers of formula I can be isolated from the reaction mixture and purified by known methodologies such as extraction, distillation, crystallization, column chromatography, and the like.

As will be apparent to those skilled in the art, the process of the present invention can be carried out using microbial cells containing an enzyme having the ability to catalyze the stereoselective transesterification of alcohols such as compounds II. When using a microorganism to perform the resolution, the present process is conveniently carried out by adding the cells and the racemic starting materials to the desired solution. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract. Cell extracts immobilized on Celite® or Accurel® polypropylene as described earlier can also be used in the transesterification reaction.

The present invention will now be described by the following examples, which are preferred embodiments of the invention and are meant to be illustrative rather than limiting.

EXAMPLE 1

1-A. trans-6-[4,4-bis(4-Fluorophenyl}-3-(1 methyl-1H-tetrazol-5-yl )-1,3-butadienyl]-tetrahydro-4-hydroxy-2H-2H-pyran-2-one This racemic alcohol 1-A was used as a substrate in the following procedures.

1-B. [4R-4α,6β(E)]]-6-[4,4-Bis(4-Fluorophenyl) -3-(1-methyl-1H-tetrazol-5-yl)-1,3-buta-dienyl]tetrahydro-4-hydroxy-2H-pyran-2-one Compound 1-A (4 grams) and isopropenyl acetate (20 ml) were dissolved in 1 liter of toluene. Crude amino lipase PS-30 from Pseudomonas sp. (10 grams), and deionized water (500 μl) were added and the reaction was conducted at 37° C., 200 RPM. The transesterification was monitored by high pressure liquid chromatography. Periodically, samples were taken, diluted 1:10 with acetonitrile and filtered through an 0.2 μm LID/X filter. 10 μl of filtered sample was injected onto a 200×4.6 mm Hypersil ODS-5 column (Hewlett-Packard) equilibrated with 60% $H_3PO_4$ and 40% acetonitrile. The samples were eluted with 60% $H_3PO_4$ and 40% acetonitrile for 12 minutes and then in a linear gradient from 60% of 0.1% $H_3PO_4$ and acetonitrile to 10% of 0.1% $H_3PO_4$ and 90% acetonitrile. The flow rate was 1 ml/min, the detection wavelength 294 nm at room temperature. The retention time for alcohol was 9.52 minutes, for acetate 16.38 minutes. The products obtained were the desired enantiomer 1-B and the acetate [4α,6β(E)]-6-[4,4-Bis-(4-fluorophenyl)-3-(1-methyl-2H-tetrazol-5-yl )-1,3-butadienyl]-tetrahydro-4-methoxycarbonyl-2H-pyran-2-one. The optical purity of resolved desired alcohol 1-B was determined on samples for analysis prepared as follows: silica gel solid phase extraction column (SPE, 200 mg bed volume) was washed with ethyl acetate followed by a 50/50 mixture of ethyl acetate/hexane. A 10 mg sample was applied to the SPE column and flushed with 7 ml of ethyl acetate/hexane (50/50). The column was flushed with 14 ml of ethyl acetate/hexane (60/40) to remove the unwanted acetylated product. Compound 1-B was eluted with 7 ml ethyl acetate/hexane (70/30), dried under a stream of $N_2$ gas, dissolved in acetonitrile/water, filtered and bottled for analysis. The retention time for the desired enantiomer 1-B was 14.91 minutes and that of the undesired enantiomer was 9.09 minutes under HPLC analysis. The kinetics of the resolution process are as shown in the Table 1. The additional 1 L reactions were conducted using the same parameters. The results were as shown in Table 2.

TABLE 1

Resolution of Compound 1-A to Compound 1-B by Pseudomonas Lipase P-30

| Reaction Time (Hours) | Reaction Yield (%) | Optical Purity of Compound 1-B (%) |
|---|---|---|
| 21 | 57.0 | 81.7 |
| 24 | 48.0 | 93.5 |
| 26 | 45.0 | 96.6 |
| 28 | 44.0 | 98.0 |
| 45 | 40.0 | 99.0 |

The reaction mixture in 1L of toluene contained 4 grams of BMY 22089, 110 grams of *Pseudomonas* lipase P-30, 20 ml of isopropenyl acetate, and 0.5 ml of deionized water. Reaction was conducted in a 1.5 L jacketed reactor at 37° C., 200 R.P.M.

TABLE 2

Resolution of Compound 1-A to Compound 1-B by Pseudomonas Lipase P-30: (1 Liter Reactor)

| Batch No. | Reaction Time (Hours) | Reaction Yield (%) | Optical Purity of Compound 1-B (%) |
|---|---|---|---|
| 1 | 15 | 40.5 | 98.6 |
| 2 | 28 | 40.5 | 99.0 |

EXAMPLE 2

Reusability of Enzyme

The substrate was racemic alcohol 1-A and desired product was resolved alcohol 1-B as described in Example 1.

Racemic alcohol 1-A (40 mg) and isoprophenyl acetate (200 μl) were dissolved in 10 ml of toluene. Crude amino lipase PS-30 from *Pseudomonas* sp (100 mg), and deionized water (5 μl) were added and the reaction was conducted at 37° C., 200 RPM on a shaker. The reaction yield and optical purity of alcohol 1-B were determined as described in example 1. After completion of the reaction, enzyme was collected by filtration and reused on the next cycle. Results of the reusability of enzyme are as shown in Table 3.

TABLE 3

Resolution of Compound 1-A to Compound 1-B by Pseudomonas Lipase P-30 Reusability of Enzyme

| Cycle No. | Reaction Time (Hours) | Reaction Yield (%) | Optical Purity of Compound 1-B (%) |
|---|---|---|---|
| 1 | 24 | 40 | 98.9 |
| 2 | 24 | 40.5 | 97.5 |
| 3 | 24 | 41 | 97.9 |

EXAMPLE 3

Immobilization of Enzyme and Use of Immobilized Enzyme

Three different carriers—XAD-7 (Amberlite XAD-7 nonionic polymeric adsorbent, 20–60 mesh polyacrylate resin) XAD-2 (Amberlite XAD-nonionic polymeric adsorbent, 20–60 mesh polystyrene resin) and Accurel PP (polypropylene resin 200–400 microns)—were used for immobilization procedures.

Crude Amano Ps 30 lipase (10 g) was dissolved in 25 ml of distilled water and centrifuged at 10,000 RPM for 10 minutes to obtain clear supernatant. The carrier (1.3 g) in a 25-ml vial was washed 5 times with methanol and added to enzyme solution in a flask and gently agitated on a gyrotory shaker at room temperature. Adsorption of enzyme to the carrier was checked periodically by lipase assay (Sigma olive oil emulsion as substrate) and by protein remaining in filtrate. About 68%, 71% and 98% adsorption efficiency were obtained using XAD-7, XAD-2, and Accurel resins, respectively. After complete immobilization (20 to 24 hours), the carrier-enzyme slurry was filtered through a Millipore filter and the carrier was washed with about 300 ml of distilled water. Subsequently, the carrier containing the immobilized lipase was dried in a vacuum oven at room temperature.

Immobilized enzyme was evaluated for the enzymatic transesterification reactions as described in Example 1. The substrate was racemic alcohol 1-A and desired product was resolved alcohol 1-B as described in Example 1.

Racemic alcohol 1-A (40 mg) and isopropenyl acetate (200 ml) were dissolved in 10 ml of toluene. Immobilized lipase (20 mg) and deionized water (50 μl) were added and the reactions were conducted at 37° C., 200 RPM on a shaker. The reaction yield and optical purity of resolved alcohol 1-B were determined as described in Example 1. The results were as shown in Table 4.

EXAMPLE 4

Use of Methyl Isobutyl Ketone and Methyl Ethyl Ketone as Solvent

The substrate was racemic alcohol 1-A and the desired product was resolved alcohol 1-B as described in Example 1.

Racemic alcohol 1-A (500 mg) and isopropenyl acetate (2.6 ml) were dissolved in 10 ml of methyl ethyl ketone (MEK) or methyl isobutyl ketone (MIBK). Crude Amano lipase PS-30 from *Pseudomonas* species (1 gram) and deionized water (10 μl) were added and the reactions were conducted at 37° C., 200 RPM on a shaker. The reaction yield and optical purity of resolved alcohol 1-B were determined as described in Example 1. The results were as shown in Table 5.

TABLE 4

Evaluation of Immobilized Enzyme in Resolution of Compound 1-A to Compound 1-B

| Immobilized Support | Reaction Time (Hours) | Reaction Yield (%) | Optical Purity (%) |
|---|---|---|---|
| XAD-2 | 42 | 39 | 98.5 |
| XAD-7 | 36 | 42 | 98.7 |
| Accurel-PP | 16 | 45 | 99 |

TABLE 5

| | Use of Methyl-Ethyl Ketone (MEK) and Methyl Isobutyl Ketone (MIBK) as Solvent in Resolution of Compound 1-A to 1-B | | |
|---|---|---|---|
| Solvent | Reaction Time (Hours) | Reaction Yield (%) | Optical Purity (%) |
| MEK | 64 | 46 | 96.4 |
| MIBK | 45 | 44 | 96.9 |

What is claimed is:

1. A process for selectively preparing a product of the formula

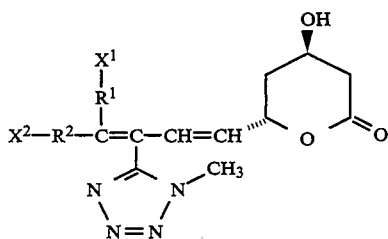

wherein $X^1$ and $X^2$ are each independently halogen and $R^1$ and $R^2$ are each independently alkyl, cycloalkyl, aralkyl or aryl; and wherein the process comprises the steps of:

(a) reacting a racemic mixture of a compound of the formula

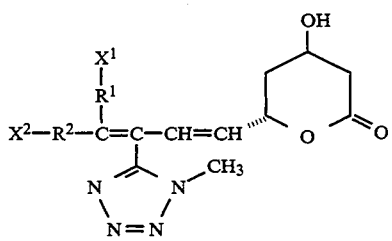

with an acylating agent of the formula

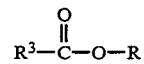

wherein R is alkyl or alkenyl and $R^3$ is alkyl, cycloalkyl, aryl or aralkyl using a *Pseudomonas lipase* or a *Pseudomonas* microorganism as a catalyst and (b) recovering the product from the reaction mixture.

2. The process of claim 1, further comprising immobilizing the enzyme or microorganism prior to the reacting step.

3. The process of claim 2, wherein the immobilizing step is carried out with XAD-2, XAD-7, or Accurel-PP as an immobilized support.

4. The process of claim 1, wherein the enzyme is present in a concentration of about 5 to 200 mg enzyme per ml of solvent.

5. The process of claim 1, wherein the reacting step is carried out in toluene, methyl isobutyl ketone, or methyl ethyl ketone.

6. The process of claim 1, wherein the process is carried out in toluene.

7. The process of claim 1, wherein the microorganism is *Pseudomonas fluorescens, Pseudomonas putida, Pseudomonas ovalis* or a lipase derived therefrom.

8. The process of claim 1, wherein the reacting step is carried out in water and an organic solvent.

9. The process of claim 1, wherein the acrylating agent is isopropenyl acetate or vinyl acetate.

10. The process of claim 1, wherein $R^1$ and $R^2$ are aryl.

11. The process of claim 1, wherein $R^1$ and $R^2$ are phenyl.

12. The process of claim 1, wherein the racemic mixture comprises trans-6-[4,4-bis(4fluorophenyl ) -3- ( 1-methyl-1H-tetrazol-5-yl) -1,3butadienyl ]-tetrahydro-4-hydroxy-2H-2H-pyran-2-one and the product is [4R-4α,6β(E)]-6-[4,4-Bis(4-fluorophenyl-3-(1-methyl-1H-tetrazol-5-yl)-1,3  -butadienyl]tetrahydro-4-hydroxy-2H-pyran-2-one.

13. The process of claim 12, wherein the acylating agent isopropenyl acetate-or vinyl acetate.

* * * * *